United States Patent
Yoshioka et al.

[11] Patent Number: 5,091,370
[45] Date of Patent: Feb. 25, 1992

[54] ANGOLAMYCIN DERIVATIVES

[75] Inventors: Takeo Yoshioka, Ayase; Azuma Watanabe, Fujisawa; Koichiro Kominato, Yamato; Hiroshi Tone, Yokohama; Rokuro Okamoto, Fujisawa; Tsutomu Sawa, Ayase; Tomio Takeuchi, Tokyo, all of Japan

[73] Assignee: Sanraku Incorporated, Tokyo, Japan

[21] Appl. No.: 539,743

[22] Filed: Jun. 18, 1990

[30] Foreign Application Priority Data

Jun. 20, 1989 [JP] Japan .................. 1-155689
Aug. 23, 1989 [JP] Japan .................. 1-214894

[51] Int. Cl.$^5$ .................. A61K 31/70; C07H 17/08
[52] U.S. Cl. .................. 514/30; 536/7.1
[58] Field of Search .................. 536/7.1; 514/30

[56] References Cited
U.S. PATENT DOCUMENTS

| | | | |
|---|---|---|---|
| 4,328,335 | 5/1982 | Mrozik | 536/7.1 |
| 4,612,372 | 9/1986 | Yoshioka et al. | 536/7.1 |
| 4,640,910 | 2/1987 | Faubl et al. | 536/7.2 |
| 4,794,173 | 12/1988 | Umezawa et al. | 536/7.1 |

Primary Examiner—Johnnie R. Brown
Assistant Examiner—Elli Peselev
Attorney, Agent, or Firm—Wenderoth, Lind & Ponack

[57] ABSTRACT

An angolamycin derivative represented by the following formula

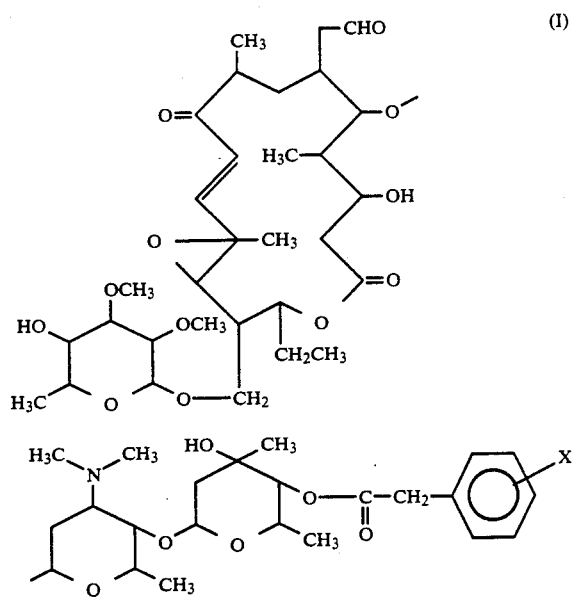

wherein X represents an acetyl, methanesulfonyl, methylthio, benzoyl or methoxy group. This compound is useful as a medicament such as antibacterial agent and an animal feed additive.

5 Claims, No Drawings

ANGOLAMYCIN DERIVATIVES

This invention relates to novel antibiotic angolamycin derivatives having an excellent antibacterial activity having a substituted phenylacetyl group at the 4″-position of the mycarose portion of macrolide antibiotic angolamycin, and important production intermediates thereof.

Macrolide antibiotics are known to have the defect that they generally have a low blood concentration and a low ratio of recovery in the urine.

Much has recently been reported, as a result of studies on the enzymatic phosphorylation, that macrolide antibiotics having a saccharide, such as mycaminose or desosamine, are inactivated by the phosphorylation of the hydroxyl group at the 2′-position hydroxyl group of such saccharides, and this phosphorylation also occurs by bacteria [such as J. Antibiotics 40, 195 (1987) and J. Antibiotics 41, 823 (1988)].

One possible cause of the low blood concentration of the macrolide antibiotic elucidated by these studies is that the 2′-hydroxyl group is phosphorylated by bacteria and consequently the macrolide antibiotic is inactivated.

On the other hand, resistant strains of the macrolide antibiotic have increased year by year. Phosphorylation may be considered to be one resistant mechanism.

It is strongly desired to develop macrolide antibiotics which are free from the defects of conventional macrolide antibiotics, such as the low recovery ratio in urine and inactivation.

It is an object of this invention to provide a macrolide antibiotic which has a high blood concentration, a good recovery ratio in urine due to resistance to inactivation, and has a high antibiotic activity.

Another object is to provide a process for producing a macrolide antibiotic in a high selectivity and high yield.

The other objects and features of the invention will become apparent from the following description.

The present inventors noted that the various defects mentioned above of macrolide antibiotics are ascribed to the phosphorylation of the 2′-hydroxyl group of mycaminose and desosamine and paid particular attention to angolamycin which is a macrolide antibiotic having angolasamine which is a saccharide without a 2′-hydroxyl group, and have made extensive investigations in order to create a derivative having a markedly strong antibacterial activity of angolamycin. As a result, the present inventors found that a novel angolamycin derivative having a substituted phenylacetyl group introduced into the 4″-position of mycarose of angolamycin has a stronger antibacterial activity than the angolamycin acyl derivative disclosed in Japanese Laid-Open Patent Publication No. 21182/1978 and possesses esterase resistance.

Thus, according to this invention, there is provided a 4″-O-substituted phenylacetylangolamycin represented by the folowing formula

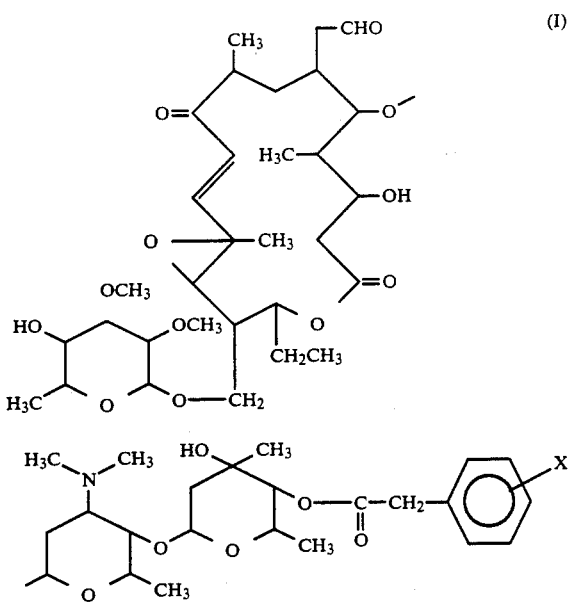

wherein X represents an acetyl, methylsulfonyl, methylthio, benzoyl or methoxy group.

In formula (I), the substituent X is preferably a methoxy, acetyl, methylthio or methylsulfonyl group. The substituent X is preferably present at the 2- or 4-position, particularly the 4-position.

According to this invention, there is provided 4‴-O-tri(lower alkyl)silylangolamycin represented by the following formula

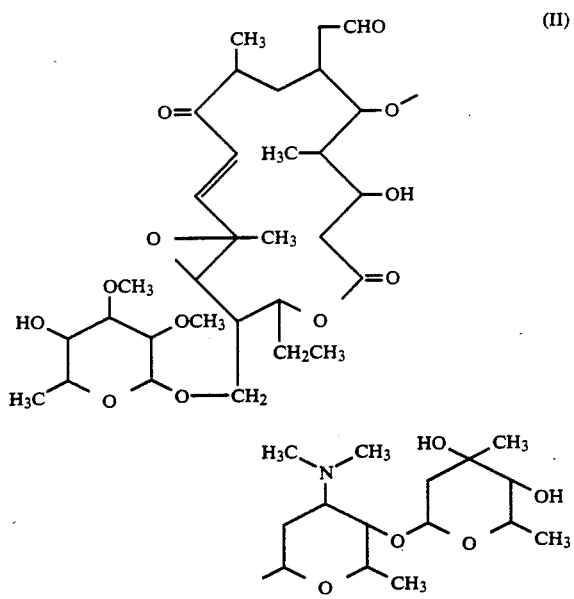

wherein R represents a tri(lower alkyl)silyl group, which is protected at the 4‴-position and which has higher reactivity than the 4″-hydroxyl group.

In the present specification, the term "lower" means that a group or a compound qualified by this term has not more than 6 carbon atoms, preferably not more than 4 carbon atoms.

Examples of the tri(lower alkyl)silyl group are tri($C_{1-6}$ alkyl)silyl groups such as trimethylsilyl, triethylsilyl, tripropylsilyl, triisopropylsilyl, tri-n-butylsilyl and tri-t-butylsilyl groups.

Typical examples of the antibiotic angolamycin derivatives of formula (I) in acccordance with this invention include
4''-O-(p-methoxyphenylacetyl)angolamycin,
4''-O-(o-methoxyphenylacetyl)angolamycin,
4''-O-(p-acetylphenylacetyl)angolamycin,
4''-O-(o-acetylphenylacetyl)angolamycin,
4''-O-(p-methylsulfonylphenylacetyl)angolamycin,
4''-O-(o-methylsulfonylphenylacetyl)angolamycin,
4''-O-(p-methylthiophenylacetyl)angolamycin,
4''-O-(o-methylthiophenylacetyl)angolamycin,
4''-O-(p-benzoylphenylacetyl)angolamycin, and
4''-O-(o-benzoylphenylacetyl)angolamycin.

Preferred among the compounds of formula (I) are 4''-O-(p-methoxyphenylacetyl)angolamycin, 4''-O-(p-acetylphenylacetyl)angolamycin, and 4''-O-(p-methylsulfonylphenylacetyl)angolamycin.

Typical examples of the 4'''-O-tri(lower alkyl)silylangolamycin derivative of formula (II) are
4'''-O-trimethylsilylangolamycin,
4'''-O-triethylsilylangolamycin,
4'''-O-tripropylsilylangolamycin,
4'''-O-triisopropylsilylangolamycin,
4'''-O-tri-n-butylsilylangolamycin, and
4'''-O-tri-t-butylsilylangolamycin.

The angolamycin derivative of formula (I) in accordance with this invention may be obtained by starting from angolamycin, protecting the 4'''-hydroxyl group which is higher in reactivity than the 4''-hydroxyl group with a suitable protective group, then acylating the 4''-position (introducing a substituted phenylacetyl group), and then eliminating the protective group at the 4'''- group.

The protection of the 4'''-hydroxyl group may be carried out, for example, by reacting angolamycin in an inert organic solvent such as an alkyl acetate solvent (e.g., ethyl acetate or butyl acetate) at a temperature of about −50° C. to about 50° C., peferably about −30° C. to about 10° C., in the presence of a suitable base such as triethylamine or imidazole with a tri(lower alkyl)halosilane, especially a tri(lower alkyl)chlorosilane such as trimethylchlorosilane. In this reaction, the amount of the tri(lower alkyl)halosilane is not strictly restricted. Generally, it is about 1 to 2 moles per mole of angolamycin.

The amount of the base which serves as an acid acceptor is also not restricted strictly. Usually the convenient amount of the base is about 1.0 to 3 equivalents per mole of angolamycin.

This reaction gives a compound of formula (II) in which the 4'''-hydroxyl group of angolamycin is protected by a tri(lower alkyl)silyl group such as a trimethylsilyl group in high selectivity and high yield.

Then, the compound of formula (II) is reacted selectively at the hydroxyl group at the 4''-position with an anhydride of a substituted phenylacetic acid of the following formula

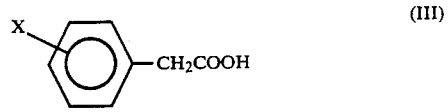

(III)

wherein X is as defined above,
or a reactive derivative thereof (such as its acid chloride or active ester) and thereafter removing the protective group at the 4'''-position by a known method, for example, by reacting it with dilute hydrochloric acid or tetra-n-butyl ammonium fluoride. Thus, the angolamycin derivatives of formula (I) can be obtained in high selectivity and in high yield. As is clearly shown in the results of in vitro tests shown below, the angolamycin derivatives of formula (I) provided by this invention, show strong antibacterial activity against pathogenic microorganisms such as Gram-positive bacteria and Gram-negative bacteria. In particular, they have strong activity against strains resistant to Staphylococcus aureus as compared against strains sensitive to it, and show excellent stability to decomposition by a liver homogenate of mice. Accordingly, the angolamycin derivatives of formula (I) provided by this invention are useful as pharmaceuticals for humans as well as animals, or as feed additives.

Antibacterial Activity Test

An antibacterial activity test was conducted in accordance with the standard method of Japan Society of Themotherapy.

The test results are shown in Tables 1 and 2.

The test compounds were:
Compound (1): 4''-O-(p-acetylphenylacetyl)-angolamycin
Compound (2): 4''-O-(p-methoxyphenylacetyl)-angolamycin
Control compound (1): 4''-O-isovaleryl angola-mycin
EM: erythromycin

TABLE 1

| (Antibacterial activity against Gram-positive and Gram-negative bacteria in general) | | | | | |
|---|---|---|---|---|---|
| Test bacteria | Compound (1) of the invention | Compound (2) of the invention | Control compound (1) | Angola-mycin | EM |
| Arthrobacter visosus ATCC 15294 | 0.39 | 0.39 | | 0.78 | 0.05 |
| Bacillus circulans ATCC 9966 | 0.05 | 0.05 | | 0.10 | <0.024 |
| B. licheniformis ATCC 25972 | 0.20 | 0.20 | | 0.20 | 50 |
| B. subtilis ATCC 6633 | 0.39 | 0.39 | 0.49 | 0.39 | <0.024 |
| Corynebacterium diphtheriae ATCC 11913 | 0.10 | 0.10 | | 1.56 | <0.024 |
| C. equi IAM 1038 | 1.56 | 3.13 | | 6.25 | 0.20 |
| Micrococcus luteus ATCC 93410 | 0.05 | | 0.10 | <0.024 | |
| Microbacterium flavum ATCC 10340 | 0.20 | 0.20 | 1.95 | 50 | |
| Sarcina lutea S19 | 0.05 | 0.05 | | 0.20 | <0.024 |
| Staphylococcus aureus 209P | 0.10 | 0.10 | 0.98 | 1.56 | 0.05 |
| S. aureus Smith | 0.20 | 0.20 | 0.49 | 1.56 | <0.024 |
| S. aureus Russell | 0.39 | 0.39 | | 1.56 | 0.05 |
| S. sp. S35 | 0.39 | 0.39 | | 3.13 | 0.05 |
| S. sp. S36 | 0.20 | 0.20 | | 1.56 | 0.05 |
| S. epidermidis ATCC 12228 | 0.39 | 0.39 | | 3.13 | 0.05 |

TABLE 1-continued (Antibacterial activity against Gram-positive and Gram-negative bacteria in general)

| Test bacteria | Compound (1) of the invention | Compound (2) of the invention | Control compound (1) | Angola-mycin | EM |
|---|---|---|---|---|---|
| Alcaligenes faecalis ATCC 8750 | >50 | >50 | | >50 | 50 |
| Alcaligenes viscolactis ATCC 9036 | 0.78 | 0.78 | | >50 | 0.10 |
| Escherichia coli NIHJ | 25 | 25 | | >50 | 25 |
| Klebsiella pneumoniae ATCC 10031 | >50 | >50 | | >50 | >100 |
| Proteus vulgaris OXKUS | >50 | >50 | | >50 | >100 |
| Pseudomonas aeruginosa IFO 3445 | >50 | >50 | | >50 | 100 |
| Ps. fluorescens SOC | 50 | >50 | | 50 | 200 |
| Salmonella gallinarum ATCC 9184 | 12.5 | 12.5 | | >50 | 12.5 |
| Sarratia marcescens IFO 3736 | >50 | >50 | | >50 | >100 |
| Shigella sonnei EW 33 | 25 | 25 | | >50 | 25 |

TABLE 2

(Antibacterial activity against macrolide-resistant S. aureus)

| Test organism | Compound (1) of the invention | Compound (2) of the invention | Control compound (1) | Angola-mycin | EM |
|---|---|---|---|---|---|
| S. aureus MS8710 | 1.56 | 1.56 | 15.6 | 6.25 | >100 |
| S. aureus MS9610 | 1.56 | 0.78 | 62.5 | >50 | >100 |
| S. aureus MS9937 | 1.56 | 0.78 | | 50 | >100 |
| S. aureus MS11588 | 1.56 | 1.56 | | >50 | >100 |
| S. aureus MS11593 | 0.39 | 0.39 | | 3.13 | >100 |
| S. aureus MS11595 | 1.56 | 0.78 | | 50 | >100 |
| S. aureus MS11597 | 0.20 | 0.39 | | 0.78 | >100 |
| S. aureus MS11598 | 0.39 | 0.39 | | 50 | >100 |
| S. aureus MS11603 | 0.20 | 0.20 | | 3.13 | >100 |
| S. aureus MS11604 | 0.39 | 0.39 | | 3.13 | >100 |
| S. aureus MS11607 | 0.39 | 0.39 | | 3.13 | >100 |
| S. aureus MS11609 | 0.20 | 0.20 | | 3.13 | >100 |
| S. aureus MS11612 | 1.56 | 1.56 | | 50 | >100 |
| S. aureus MS11614 | 1.56 | 0.78 | | 25 | >100 |
| S. aureus MS11627 | 0.39 | 0.39 | | 50 | >100 |
| S. aureus MS11629 | 1.56 | 0.78 | | 50 | >100 |
| S. aureus MS11630 | 1.56 | 0.78 | | >50 | >100 |
| S. aureus MS11636 | 0.78 | 0.78 | | 3.13 | >100 |
| S. aureus MS8598 52A(S7) | 1.56 | 1.56 | | >50 | >100 |
| S. aureus MS8800 52 75(S9) | 1.56 | 1.56 | | >50 | >100 |
| S. aureus MS8900 (S12) | 0.78 | 0.78 | | >50 | >100 |
| S. aureus MS8908 80 81 | 0.78 | 0.39 | | 50 | >100 |
| S. aureus Sa-52 (S32) | 0.78 | 0.78 | | 25 | >100 |

Stability test against a mouse liver homogenate

The livers of ICR-strain mice were homogenized together with 5 times their amount of 0.1M phosphate buffer (pH 7.2) in a Potter homogenizer (3000 rpm, 10 minutes). One ml of 500 micrograms/ml of a test compound (10% methanol water) was added to the supernatant (1 ml) of the homogenate, and reacted at 37° C. for 1 hour. The mixture was heated at 100° C. of 3 minutes. Then, 1 ml of 0.1M phosphate buffer (pH 9.0) was added, and the mixture was extracted with 1 ml of ethyl acetate, organic layer was subjected to silica gel thin-layer chromatography (chloroform/methanol/ammonia=15/1.2/0.1), and by a chromatoscanner (283 nm), the ratio of an unchanged product and a hydrolyzed product formed was determined. The amount of the unchanged product remaining was expressed by percentage. The results are shown in Table 3.

TABLE 3

| | Stability against mouse liver homogenate | | |
|---|---|---|---|
| Compound | Compound (1) (1) of the invention | Compound (2) (2) of the invention | Control compound (1) |
| Residual activity | 94 | 95 | 55 |
| ratio (%) | | | |

Homogenizing time: 60 minutes

It is clearly seen from the results of the in vitro tests that the angolamycin derivatives of formula (I) have excellent antibacterial activity and show strong antimicrobial activity against resistant strains, and are stable to esterase. Because of the above properties, the present substances are very useful as antibacterial agents for humans as well as for animals and as feed additives.

When the compounds of formula (I) are to be used as an antibacterial agent, for example for treatment and medication of infections, they may be administered to warm-blooded animals orally, parenterally (e.g., intramuscular and subcutaneous) or topically, particularly preferably orally.

When the compounds of the invention are to be used as a medicament, they may be formulated together with a pharmaceutically acceptable carrier or diluent into forms suitable for oral, parenteral or topical administration. For example, the compounds of this invention may be formulated by using conventional nontoxic adjuvants, such as a vehicle, a binder, a lubricant, a disintegrant, an antiseptic, an isotonizing agent, a stabilizer, a dispersing agent, an antioxidant, a coloring agent, a corrigent, and a buffer.

Such medicament may be in a solid form (e.g., tablets, soft capsules, hard capsules, granules, a powder, pellets, pills, or trouches), a semisolid form (e.g., a suppository, an ointment, or a cream) and a liquid form (e.g., an emulsion, a suspension, a syrup, or a spray).

The final prescription of a feed for an animal or poultry depends upon the amount of the drug to be administered.

The most practical method of administering of the compound of this invention is to add it to the feed or drinking water. Various feeds such as normal dried feeds, liquid feeds and granular feeds may be used.

A method of prescribing the drug in an animal feed is well known. A suitable method is to prepare a concentrated drug premix for production of a drug-added feed. An ordinary premix contains about 1 to about 200 g of the drug per pound of the premix. The premix may be in the form of a liquid or solid preparation.

Examples of non-toxic inert carrier or diluent that can be used include starch, gelatin, glucose, lactose, fructose, maltose, magnesium carbonate, magnesium metasilicate aluminate, synthetic aluminium silicate silicic anhydride, talc, Eudragit, magnesium stearate, methyl cellulose, carboxy methyl cellulose, carboxy methylethyl cellulose, or its salt, gum arabic, polyethylene glycol, alkyl p-hydroxybenzoates, syrup, ethanol, propylene glycol, Vaseline, carbowax, glycerol, sodium chloride, sodium sulfite, sodium phosphate, citric acid and buffers.

The amount of the compound of this invention in the medicament may be varied according to its form, but is generally desirably 25 to 100% by weight, for a solid or semisoild form, and 0.01 to 2.0% by weight for a liquid form.

The dosage of the compound of this invention may be varied widely depending upon the subject to which it is administered, the administration route, the severity of the condition, the body weight of the subject, and the diagnosis of the physician, etc. Generally, it may be 2 to 200 mg/kg, preferably 5 to 50 mg/kg. The above dosage is a tentative measure, and may be larger or less than the specified limit depending upon the severity of the subject, the physicians' judgment, etc. The above dosage may be administered once or in several divided doses per day.

The following examples further illustrate the present invention specifically.

EXAMPLE 1

Synthesis of 4″-O-(p-methoxyphenylacetyl)-angolamycin

Angolamycin (186 mgg; 0.203 mmole) was dissolved in 1.9 ml of ethyl acetate. The solution was cooled to −20° C. Triethylamine 62.2 microliters (0.447 mmole) and triethylchlorosilane 51.5 microliters (0.406 mmole) were added, and the mixture was stirred at the above temperature for 2 hours. The reaction mixture was diluted with 10 ml of ethyl acetate, and washed with 5 ml of a saturated aqueous solution of sodium hydrogen carbonate, and further with 5 ml of a saturated aqueous solution of sodium chloride. The organic layer was dried over anhydrous sodium sulfate. The desiccant was removed, and the residue was concentrated under reduced pressure to give 175 mg (yield 87%) of 4‴-O-trimethylsilylangolamycin.

Its physico-chemical properties are shown below.

$IR\nu_{max}^{CHCl_3}$ cm$^{-1}$: 2920, 1720, 1685, 1620

$^1$H-NMR(CDCl$_3$, δppm from TMS): 0.20(9H, s, OSi(CH$_3$)$_3$), 1.45(3H, s, 12-CH$_3$), 2.28(6H, s, 3′—N(CH$_3$)$_2$), 3.58(3H, s, 2‴-OCH$_3$), 3.62(3H, s, 3‴—OCH$_3$), 4.63(1H, d, J=7.5 Hz, H$_1$‴), 5.05(1H, br, H$_1$″), 5.35(1H, m, H$_{15}$), 6.45(1H, d, J=15 Hz, H$_{10}$), 6.60(1H, d, J=15 Hz, H$_{11}$), 9.78(1H, s, CHO).

EXAMPLE 2

51.4 mg (0.052 mmole) of 4‴-O-trimethylsilylangolamycin obtained in Example 1 was dissolved in 1 ml of methylene chloride. The solution was cooled to −30° C., and 15.4 microliters (0.110 mmole) of triethylamine and 0.6 mg of 4-dimethylaminopyridine were added Furthermore, 0.5 ml of a methylene chloride solution containing 32.7 mg (0.104 mmole) of p-methoxyphenylacetic anhydride was added dropwise gradually. The reaction mixture was stirred at the above temperature for 1 hour, diluted with 10 ml of methylene chloride, washed twice with 6 ml of a saturated aqueous solution of sodium hydrogen carbonate and with 5 ml of a saturated aqueous solution of sodium chloride. The organic layer was dried over anhydrous sodium sulfate. The desiccant was removed, and the residue was concentrated under reduced pressure and subjected to silica gel column chromatography (1.4 g). Elution with toluene/acetone (5/1, 3/1, 2/1) gave 4″-O-(p-methoxyphenylacetyl)-4‴-O-trimethylsilylangolamycin in an amount of 26.8 mg (yield 45%).

Its physico-chemical properties are shown below.

$IR\nu_{max}^{CHCl_3}$ cm$^{-1}$: 2925, 1720, 1690, 1620

$^1$H-NMR(CDCl$_3$, δppm from TMS): 0.20(9H, s, OSi(CH$_3$)$_3$), 1.48(3H, s, 12—CH$_3$), 2.27(6H, s, 3′—N(CH$_3$)$_2$), 3.55(3H, s, 2‴—OCH ), 3.61(3H, s, 3‴-OCH$_3$),

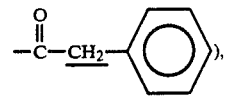

4.58(1H, d, J=10 Hz, H$_4$″), 5.05(1H, d, J=3 Hz, H$_1$″), 5.33(1H, m, H$_{15}$), 6.42(1H, d, J=15 Hz, H$_{10}$), 6.60(1H, d, J=15 Hz, H$_{11}$),

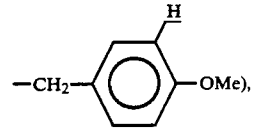

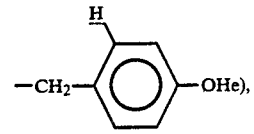

9.73(1H, s, CHO).

The resulting 4″-O-(p-methoxyphenylacetyl)-4‴-O-trimethylsilylangolamycin (12.5 mg) was dissolved in 1 ml of acetone. Under cooling, 1 ml of 0.025N hydrochloric acid was added dropwise gradually, and the mixture was stirred at the above temperature for 1 hour. The reaction solution was diluted with 10 ml of ethyl acetate, washed with 5 ml of a cold saturated aqueous solution of sodium hydrogen carbonate and 5 ml of a saturated aqoues solution of sodium chloride, and dried over anhydrous sodium sulfate. The desiccant was removed, and the residue was concentrated under reduced pressure. The residue was subjected to silica gel column chromatography (1 g), and eluted with toluene-/acetone (4/1, 3/1, 2/1) to give 6.7 mg (yield 57%) of 4''-O-(p-methoxyphenylacetyl)angolamycin.

The product had the following physicochemical properties.

Specific rotation $[\alpha]_D^{23}$: −58.4° (C 0.5, CHCl$_3$)
UV$\lambda_{max}^{MeOH}$ nm($\epsilon$): 231(17000)
IR$\nu_{max}^{CHCl_3}$ cm$^{-1}$: 1920, 1720, 1685, 1620

$^1$H-NMR(CDCl$_3$, δppm from TMS): 1.45(3H, s, 12-CH$_3$), 2.27(6H, s, 3'-N(CH$_3$)$_2$), 3.56(3H, s, 2'''-OCH$_3$), 3.62(3H, s, 3'''-OCH$_3$),

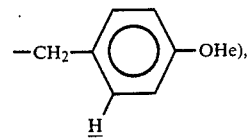

9.70(1H, s, CHO)
SI-MS (m/z): 1064(M$^+$+1)
$^{13}$C-NMR (CDCl$_3$): δ=9.2(C-17), 9.5(C-18), 15.0(C-22), 17.4(C-21), 17.7(C-6''), 17.8(C-6'''''), 18.9(C-6'), 24.7(C-16), 25.2(C-7''), 27.3(C-2'), 31.3(C-6), 31.4(C-7), 39.7(C-2), 40.4(C-2''''), 40.8(NMe$_2$), 41.1(C-4), 41.6(C-2''), 43.6(C-14), 43.6(C-19), 45.0(C-8), 55.3(6'''''-OMe), 59.4(C-12), 59.7(2'''-OMe), 61.7(3'''-OMe), 63.3(C-5''), 64.0(C-3'), 64.2(C-13), 66.4(C-3), 67.3(C-23), 69.4(C-3''), 70.8(C-5'''), 72.6(C-4'), 73.2(C-5'), 73.9(C-15), 75.8(C-4'''), 77.7(C-4''), 79.6(C-3'''), 81.6(C-5), 81.9(C-2'''), 97.1(C-1''), 101.0(C-1'''), 101.8(C-1'), 113.9(C-5''''') 122.6(C-10), 126.0(C-3''''), 130.4(C-4''''), 151.2(C-11), 158.7(C-6'''''), 171.8(C-1''''), 173.2(C-1), 200.1(C-9), 202.7(C-20).

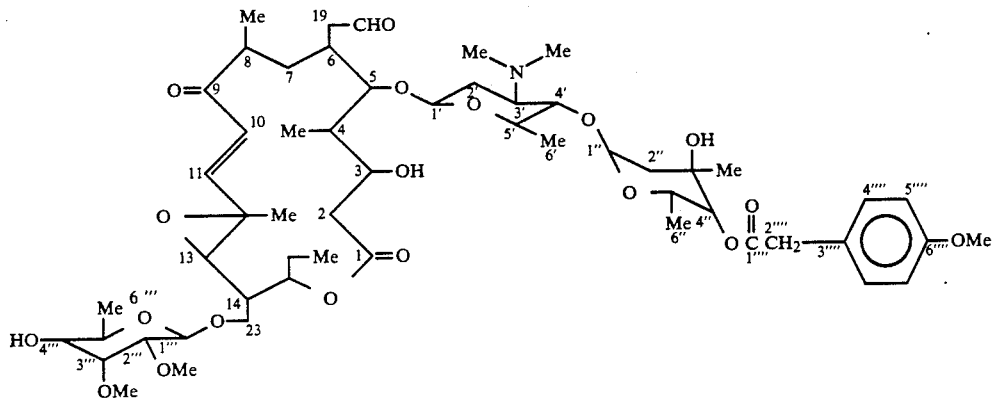

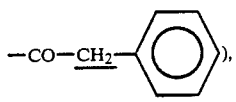

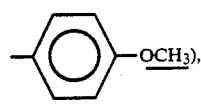

4.57(1H, d, J=8 Hz, H$_1$'''), 4.58(1H, d, J=10 Hz, H$_4$''), 5.05(1H, d, J=3 Hz, H$_1$''), 5.33(1H, dt, J=10 and 2.5 Hz, H$_{15}$), 6.44(1H, d, J=15 Hz, H$_{10}$), 6.57(1H, d, J=15 Hz, H$_{11}$),

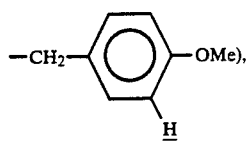

EXAMPLE 3

Syhnthesis of 4''-O-(p-acetylphenylacetyl)-angolamycin 60.9 mg (0.0616 mmole) of 4'''-O-trimethylsilylangolamycin produced by the same method as in Example 1 was dissolved in 0.6 ml of methylene chloride, and 56 microliters (0.0377 mmole) of triethylamine and 4.6 mg (0.0377 mmole) of 4-dimethylaminopyridine were added and the mixture was cooled to −30° C. A methylene chloride solution of p-acetylphenylacetic acid treated in advance with 30 microliters (0.246 mmole) of pivaloyl chloride and 29 microliters (0.208 mmole) of triethylamine was added to the resulting solution. The mixture was stirred at −30° C. for 3 hours. A saturated aqueous solution of sodium hydrogen carbonate was added to the reaction mixture, and its temperature was returned to room temperature. A small amount of methylene chloride was added to extract it. The methylene chloride layer was washed further with a saturated aqueous solution of sodium hydrogen carbonate and a saturated aqueous solution of sodium chloride in this order. It was then dried over anhydrous sodium sulfate, and concentrated under reduced pressure. The residue was subjected to silica gel column chromatography (3 g), and eluted with toluene/acetone (8/1, 5/1, 3/1) to give 26.1 mg (yield 36.9%) of 4''-O-(p-acetylphenylacetyl)-4'''-O-trimethylsilyl angolamycin.

The resulting product had the following physicochemical properties.

IR$\nu_{max}^{CHCl_3}$ cm$^{-1}$: 3430, 2920, 1720, 1680, 1615

$^1$H-NMR(CDCl$_3$, δppm from TMS): 0.17(9H, s, OSi(C$_3$)$_3$), 1.43(3H, s, 12-CH$_3$), 2.26(6H, s, 3'-N(CH$_3$)$_2$).

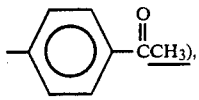

3.55(3H, s, 2'''—OCH$_3$), 3.60(3H, s, 3'''—OCH$_3$),

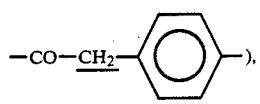

4.59(1H, d, J=9 Hz, H$_1$'''), 4.61(1H, d, J=11 Hz, H$_4$''), 5.05(1H, br, H$_1$'''), 6.40(1H, d, J=16 Hz H$_{10}$), 6.62(1H, d, J=16 Hz H$_{11}$),

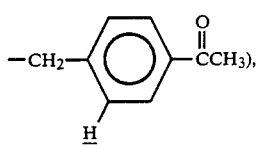

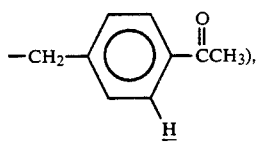

9.74(1H, s, CHO).

The resulting 4''-O-(p-acetylphenylacetyl)-4'''-O-trimethylsilylangolamycin 8.7 mg (0.00757 mmole) was dissolved in 0.5 ml of acetone, and under ice cooling, 0.4 ml of 0.025N hydrochloric acid. The mixture was stirred at the above temperature for 2.5 hours and diluted with a small amount of ethyl acetate. The solution was washed with a saturated aqueous solution of sodium hydrogen carbonate and a saturated aqueous solution of sodium chloride in this order. The solution was dried over anhydrous sodium sulfate, and concentrated under reduced pressure. The resulting residue was purified by preparative thin-layer chromatography [developing solvent system: toluene/acetone=4/1 (V/V)] to give 3.2 mg (yield 39.3%) of 4''-O-(p-acetylphenylacetyl)-angolamycin.

The resulting product had the following physicochemical properties.

Specific rotation [α]$_D^{21}$: −54.2° (C 0.71, CHCl$_3$)

UVλ$_{max}^{CH_3OH}$ nm(ε): 246(27000)

IR$_{max}^{CHCl_3}$ cm$^{-1}$: 3450, 2920, 1720, 1680, 1615

$^1$H-NMR(CDCl$_3$, δppm from TMS): 1.44(3H, s, 12-CH$_3$), 2.26(6H, s, 3'-N(CH$_3$)$_2$),

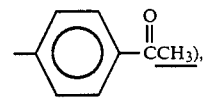

3.58(3H, s, 2'''—OCH$_3$), 3.64(3H, s, 3'''—OCH$_3$),

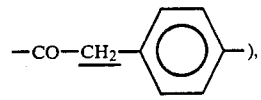

4.58(1H, d, J=7 Hz, H$_1$'''), 4.60(1H, d, J=11 Hz, H$_4$''), 5.06(1H, br, H$_1$''), 6.41(1H, d, J=16 Hz H$_{10}$), 6.62(1H, d, J=16 Hz H$_{11}$),

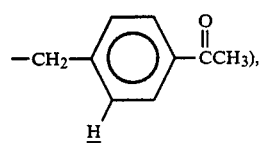

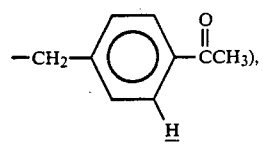

8.73(1H, s, CHO)

SI-MS (m/z): 1076(M$^+$+1).

EXAMPLE 4

100 g of the antibiotic I prepared as above and 50 g, 20 g, 10 g or 5 g of Eudragit E100 were dissolved in 300 ml of methylene chloride. The solution was spray-dried at 80° C. by a spray-drying machine to obtain a powdery dispersion.

EXAMPLE 5

Crystalline cellulose (150 g) was put in a fluidized layer granulating drying machine. Separately, 200 g of the antibiotic I and 40 g of Eudragit E100 were dissolved in 600 ml of methylene chloride at 20° C. The solution was sprayed onto crystalline cellulose nuclei, and granulated and dried at 40° C. for 60minutes. Carboxymethyl cellulose (100 g) was uniformly mixed. The mixture was filled in #3 capsules to obtain a capsular agent.

EXAMPLE 6

Crystalline cellulose (96 g) and carboxymethyl cellulose (80 g) were put in a fluidized layer granulating drying machine. 200 g of the antibiotic I and 20 g of Eudragit E100 were dissolved in 600 ml of methylene chloride at 30° C. The solution was granulated. Magnesium stearate (4.5 g) was mixed. The mixture was tableted to obtain tablets (10 mm in diameter; 200 mg potency/tablet).

EXAMPLE 7

Crystalline cellulose (20 g), 80 g of carboxymethyl cellulose, 40 g of corn starch and 20 g of carboxymethylethyl cellulose were put in a fluidized layer granulating drying machine. Separately, 200 g of antibiotic I and 20 g of Eudragit E100 were dissolved in 600 ml of methylene chloride at 30° C., and granulated. The granules were mixed with 8 g of magnesium stearate, and the mixture was tableted to obtain tablets (10 mm in diameter; 200 mg potency/tablet).

EXAMPLE 8

One hundred grams of the antibiotic I and 50 g, 20 g, 10 g or 5 g of carboxymethylethyl cellulose were dissolved in 300 ml of a mixture of methylene chloride and ethanol (1:1) at 25° C. The solution was sprayed at 80° C. to form a powder. It was mixed with 100 g of crystalline cellulose and 2 g of magnesium stearate, and granulated by a dry granlator. The particle size was adjusted to form granules having a size of 24 to 80 mesh.

EXAMPLE 9

Prescription (for one capsule)

Antibiotic I 59 mg

Lactose 200 mg

Magnesium stearate 0.4 mg

Method

The antibiotic I, lactose and magnesium stearate were mixed. The mixture was filled into #2 capsules to form capsular agents.

We claim:

1. An angolamycin derivative represented by the following formula

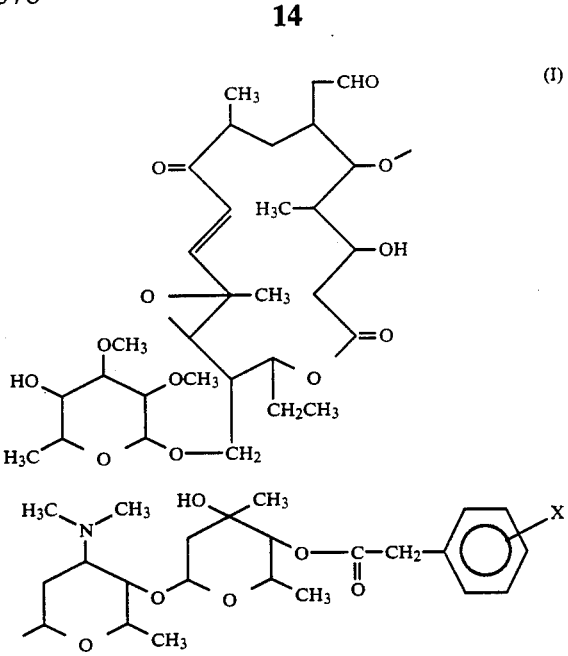

wherein X represents an acetyl, methylsulfonyl, methylthio, benzoyl or methoxy group.

2. The compound of claim 1 in which the substituent X is bonded to the 2- or 4-position on the phenyl ring.

3. The compound of claim 1 which is selected from the group consisting of 4''-O-(p-methoxyphenylacetyl)angolamycin, 4''-O-(p-acetylphenylacetyl)angolamycin, and 4''-O-(p-methylsulfonylphenylacetyl)angolamycin.

4. A pharmaceutical composition comprising an antibacterially effective amount of the angolamycin derivative represented by formula (I) in claim 1, and a pharmaceutically acceptable carrier or diluent.

5. A method of treating a patient suffering from a bacterial infection, which comprises administering to said patient an antibacterially effective amount of the angolamycin derivative of formula (I) in claim 1.

* * * * *